United States Patent [19]

Upham et al.

[11] 4,006,219

[45] Feb. 1, 1977

[54] COMPOSITION AND METHOD FOR COUNTERING EFFECTS OF ALCOHOL CONSUMPTION

[75] Inventors: John S. Upham, Clearwater; R. Scott Grybek; Theodore R. Raulerson, Jr., both of Tampa, all of Fla.

[73] Assignee: Ceres Pharmacal Company, Des Moines, Iowa

[22] Filed: Jan. 29, 1975

[21] Appl. No.: 545,041

Related U.S. Application Data

[63] Continuation of Ser. No. 279,338, Aug. 10, 1972, abandoned.

[52] U.S. Cl. .................... 424/94; 424/252; 424/255; 424/266
[51] Int. Cl.² ............ A61K 31/51; A61K 31/455; A61K 31/525; A61K 37/48
[58] Field of Search ............ 424/252, 255, 266, 94

[56] References Cited

UNITED STATES PATENTS 2,477,491  7/1949  Miller .................. 424/255
3,011,944  12/1961  Yamashita .................. 424/252
3,037,911  6/1962  Stoyle .................. 424/252

OTHER PUBLICATIONS

Conn—Current Therapy (1970) pp. 613–617.
Goodman & Gilman — The Pharmacological Basis of Theropeutics; 2nd Ed. (1955) pp. 1697 & 1696 British Medical Journal — Nov. 21, 1964 pp. 1290–1292.
Physician's Desk Reference (1971) pp. 969 & 1435.

*Primary Examiner*—Stanley J. Friedman
*Attorney, Agent, or Firm*—Neuman, Williams, Anderson & Olson

[57] ABSTRACT

A composition and method for countering the effects of alcohol consumption by a person. The composition includes a specifically proportioned combination of thiamine, riboflavin, niacin and yeast, preferably in tablet form. The method includes orally administering the composition to a person under the influence of alcohol.

18 Claims, No Drawings

COMPOSITION AND METHOD FOR COUNTERING EFFECTS OF ALCOHOL CONSUMPTION

This is a continuation of application Ser. No. 279,338 filed Aug. 10, 1972, now abandoned.

BACKGROUND OF THE INVENTION

It is an indisputable fact that a substantial segment of the world's population periodically is under the influence of alcohol, to varying degrees and for a variety of reasons. It is not our purpose to become involved in the moral aspects of alcohol consumption, or to delve into philosophical questions concerning the relative amounts of pleasure and pain experienced by people in general as a result of alcohol consumption. It is rather our purpose to mitigate or eliminate, to a significant degree, the most obvious physical effects of alcohol consumption.

Broadly, the two most obvious effects of alcohol consumption are intoxication, and what is commonly referred to as hang-over. Either of these effects may be experienced over a wide spectrum, ranging from barely noticeable to severe. For many years, efforts have been made to find methods or means to counter these effects. Unfortunately for the drinking public, and also for non-drinkers who may be adversely affected by members of the drinking public, previous attempts to counter the effects of alcohol consumption have generally been ineffective, or at best only of limited effect.

No attempt will be made to document all the previous attempts to counter the effect of alcohol consumption, but a few of the more popular methods will be briefly discussed to provide a reference framework. The most popular method of treating an intoxicated person, in an effort to sober the person up quickly, probably is to have the person drink coffee. Unfortunately, coffee has no significant effect on the state of intoxication, and the primary effect of coffee is to change a sleepy drunk into a wide-awake one. It has generally been accepted that the only effective remedy for intoxication is time. That is, the body must be given time to metabolize the alcohol in the blood stream and body tissues. No satisfactory manner of speeding up the process is presently known.

Ethyl alcohol is a carbohydrate. Carbohydrates are metabolized through what is known as the "Krebs Cycle" or the "Citric Acid Cycle." Ethyl alcohol causes intoxication, and an enzyme known as alcohol dehydrogenase, which is produced in the liver, breaks the ethyl alcohol down to carbon dioxide and water. The secondary effect or hangover is thought to result from oxidation of the alcohol which causes a speed up in breathing, heart action and muscle action which breaks down blood sugar to lactic acid. An enzyme known as lactic acid dehydrogenase reverses this process, and converts lactic acid back to blood sugar, thereby eliminating the hangover.

As to methods of relieving the after-effects of alcohol consumption (hangover), their number is great, and they range from various concoctions of food, beverage or medicine to such things as breathing concentrated oxygen. While certain of these methods provide a degree of relief for some people, unfortunately nothing to date is completely and satisfactorily effective.

One of the greatest present problems involving persons who consume alcoholic beverages is that they often unwittingly reach a degree of intoxication greater than desirable for the activity they plan to engage in after cessation of alcohol consumption.

Thus, there is obviously a need for something that will counter the effects of alcohol consumption quickly and effectively, and such is provided by this invention.

SUMMARY OF THE INVENTION

According to this invention, a composition and method are provided for countering the effects of alcohol consumption. More specifically, a composition containing a combination of ingredients in specific proportions is provided, which when administered to a person after consumption of alcoholic beverage can reduce or eliminate the effects of intoxication and hang-over quickly and dramatically.

The composition includes thiamine, riboflavin, niacin, and preferably an edible yeast. The composition preferably is in tablet form, but may be powdered and prepared as a slurry or liquid suspension shortly before use, or may be a capsule containing the ingredients. Also, the composition could be in the form of a canned fluid.

The method comprises orally administering an effective amount of the composition to a person, preferably shortly after cessation of consumption of alcoholic beverage.

DESCRIPTION OF THE PREFERRED EMBODIMENTS

The following detailed descriptions of preferred embodiments of the invention, including examples, will illustrate the best known versions of the invention, but it should be noted that additional variations and modifications would fall within the actual scope of the invention.

Certain terms are used throughout the specification and claims which should be defined at this point. Thiamine is intended to represent vitamin $B_1$, or thiamine as the hydrochloride or mononitrate salts. Thiamine is readily available from a number of sources, either as a natural or synthetic product, and generally is in a powder form. Riboflavin, or vitamin $B_2$, is similarly available in natural or synthetic form as a powder. Niacin is used to mean nicotinic acid, and is sometimes referred to in the art as anti-pellagra vitamin. As used herein, the term yeast is used to define any pharmaceutically suitable yeast or extract thereof and includes substances sometimes referred to as edible yeasts, brewers yeast, pasteurized yeast, etc. A specific example of a preferred yeast is *Saccharomyces cerevisiae*, but many others are equally applicable.

The term "alcohol" as used herein always refers to ethyl alcohol, and "alcoholic beverage" refers to any of the popular spirits or blends containing ethyl alcohol and intended for human consumption. When reference is made to a volume of alcohol consumed, unless indicated otherwise the amount has been calculated as actual ethyl alcohol volume, rather than volume of a liquor. In the following tests, however, commercially available liquors were used.

The following examples are representative of a large number of tests illustrating the dramatic effects obtainable from this invention. It will be appreciated that both intoxication and hang-over are relative terms, not generally amenable to precise measurement or description. Nevertheless, despite the subjective nature of the tests the dramatic effect of the invention is clearly apparent.

It should also be pointed out that the following examples do not represent all the results of tests that were performed. In some cases, the subjects showed little or no beneficial effect from the invention, particularly in cases where the test subject had consumed enough alcohol to be at or near the "passed-out" condition. Also, due to undetermined differences in individual persons tested, certain persons simply did not make satisfactory test subjects. It will be appreciated that the testing procedure was complicated by the fact that in many cases the testing area initially was occupied by a substantial number of intoxicated persons who interacted.

However, in most cases where the tests were not completely or substantially demonstrative of the sobering effect of the invention, the failure could be traced to a quality control problem such as improper formulation or handling of the composition. For example, the composition loses effectiveness if subjected to excessive heat, light, oxygen or moisture over a period of time. Also, the inclusion of interfering or inhibiting materials during compounding or formulation in some cases resulted in loss of effectiveness.

The composition of the invention includes, as essential ingredients, thiamine, riboflavin and niacin (nicotinic acid). The preferred embodiment of the invention also includes yeast, although in at least one test successful results were obtained with a yeast-free composition. Preferred versions of the invention include thiamine and riboflavin in about equal amounts, and niacin in about one third the amount of either thiamine or riboflavin.

The upper limit of thiamine and ribofavin which a person can consume without harm is thousands of times higher than the estimated daily requirement, and within the framework of the levels used in this invention toxicity is not a consideration. Niacin (nicotinic acid) is relatively non-toxic, but vasodilation, seen as intense flush of the skin, may follow oral intake of excessive amounts of niacin. Partly for this reason, the niacin content of the composition of the invention is preferably only about one third that of the thiamine or riboflavin. The yeast is recognized as a nutritionally excellent substance.

It should be pointed out that while various vitamin preparations or supplements are widely available which include, among other ingredients, part or all of the essential elements of this composition, the products in fact are neither similar nor even related to the composition of this invention. The levels of the critical components of this composition are much higher than the levels found in the common supplemental vitamin formulations, which would be essentially ineffective for the purpose of this invention.

While it is not known for certain just what the mechanism of the reduction in intoxication is, it has been demonstrated dramatically in the following tests.

EXAMPLE I

In this example, eight persons each consumed a distilled alcoholic liquor (average 86 proof) in amounts of from 3 to 9½ fluid ounces over a relatively short period of time. Shortly after cessation of alcohol consumption, a slurry containing 120 mg thiamine, 120 mg riboflavin, 40 mg niacin, and 1520 mg yeast was orally administered to each of the test subjects who were in varying states of intoxication. Within 40 minutes, all but one of the persons had "good" restoration of mental and physical faculties. The one exception was observed to have "fair" restoration of mental and physical faculties within 65 minutes.

EXAMPLE II

In this example, twelve persons each consumed between 3.4 and 9.5 ounces of a distilled alcoholic liquor (average 86 proof) within a relatively short time, and reached varying degrees of intoxication. Shortly after cessation of alcohol consumption, four tablets, each containing 34 mg thiamine, 34 mg riboflavin, 11 mg niacin, 300 mg yeast, 25 mg corn starch, 15 mg gum arabic and 70 mg microcrystalline cellulose were orally administered to the test subjects. In less than one hour, all but one of the test subjects had made good recovery of mental and physical faculties. The other subject made fair recovery.

The inclusion of corn starch, gum arabic and microcrystalline cellulose in the tablets was strictly for aiding in tablet formation, and these ingredients are considered inert and not as contributing to the effect of the composition. Equivalent materials, such as other forms of starch or gums, might be substituted, the only requirement being that such materials be inert as to the proper performance of the esssential ingredients of the invention.

EXAMPLE III

In this example, five persons each consumed from 4.7 to 12.3 ounces of distilled alcoholic liquor (average 86 proof) over a relatively short period of time, reaching varying degrees of intoxication. Shortly after cessation of alcoholic consumption, four tablets each containing 34 mg thiamine, 34 mg riboflavin, 11 mg niacin and 50 mg starch were orally administered to each person. In this test, no yeast was present in the tablets. Within 26 minutes of taking the tablets, four of the persons, including one who had consumed 12.3 ounces of liquor, had good restoration of both mental and physical faculties. The remaining person had good restoration after 30 minutes.

EXAMPLE IV

This example is illustrative of the type of test performed on several hundred subjects, and is representative of the results obtained. The subject, a male person weighing 140 pounds, consumed 200 ml of Scotch whisky over a period of 48 minutes. Approximately 30 minutes after cessation of alcoholic consumption, and while the subject was seriously intoxicated, he was given four tablets each containing 34 mg thiamine, 34 mg riboflavin, 11 mg niacin, 300 mg yeast, 25 mg starch, 15 mg gum arabic and 70 mg microcrystalline cellulose. The subject was observed as to ability to sit, walk, stand, talk and see, and was questioned as to numbness of face and extremities, fuzzy eyesight, thickness of tongue, and general condition. Within 24 minutes of taking the tablets, the subject felt that his degree of intoxication had noticeably lessened. This was confirmed by observation. Within slightly less than 1 hour, the subject appeared to be, and felt himself to be, substantially sober.

In the above tests, the observations as to recovery of faculties involved subjectively evaluating such things as speech, visual changes, light mental exercise, motor coordination, and comparative writing, drawing, etc.

In addition to the above tests, several hundred additional persons were similarly tested using varying total amounts and proportions of the essential ingredients of the invention. These tests indicated that in instances where the test formulation had not deteriorated, such as happened in certain cases due to inadvertent overexposure to light, heat, air or moisture, a composition containing at least 40 mg thiamine, at least 40 mg riboflavin, and from 10 to 80 mg niacin was effective in most cases in dramatically countering the intoxicating effect of alcohol. The use of more than about 200 mg of thiamine or riboflavin, while effective, provided no significant improvement in effect over the use of lesser, but effective, amounts. The inclusion of from 800 to 1600 mg of yeast was observed to generally result in more consistent results. The reduction of hang-over effect, while obviously subjective, was consistently noted by the test subjects.

The addition of starch, gums, microcrystalline cellulose and equivalent materials, inert as to the proper performance of the essential ingredients of the invention, may desirably be added for purposes of forming tablets.

The composition, whether in tablet form or otherwise, should be protected from overexposure to heat, light, moisture and oxygen. The composition in tablet form is desirably packaged in a sealed container under controlled conditions to insure maximum shelf life.

It is again pointed out that the above examples are exemplary, are illustrative of the preferred embodiments of the invention as determined by extensive testing, and are not to be considered as limiting the invention. Neither are they to be construed as representing that the invention is always effective regardless of the amount of alcohol consumed or of other factors. They do describe the invention in the most preferred form known, and they are representative of the dramatic and surprising results obtainable from the invention.

We claim:

1. A method of reducing the intoxicating effects associated with the consumption of beverage ethyl alcohol by a person which comprises orally administering to said intoxicated person a composition consisting essentially of at least about 30 mg. thiamine, at least about 30 mg. of riboflavin and at least about 10 mg. of niacin, and up to 2000 mg. of yeast in a dosage unit.

2. A method according to claim 1 wherein the dosage unit administered contains from 30 to 200 mg. of thiamine, 30 to 200 mg. of riboflavin and from 10 to 80 mg. of niacin.

3. A method according to claim 1 wherein the composition contains at least 40 mg. of thiamine, at least 40 mg. of riboflavin, and from 10 to 80 mg. of niacin.

4. A method according to claim 1 wherein the thiamine, riboflavin and niacin are present in the composition in ratios of about 3 parts thiamine, 3 parts riboflavin and 1 part niacin.

5. The method of claim 1 wherein the composition is administered in the form of a plurality of tablets.

6. The method of claim 1 wherein the composition contains from 120 to 140 mg thiamine, from 120 to 140 mg riboflavin, about 40 mg niacin, and from 800 to 1600 mg yeast per dosage unit.

7. The method of claim 1 wherein the composition administered consists of four tablets each containing from 30 to 35 mg thiamine, from 30 to 35 mg riboflavin, about 10 mg niacin, and about 300 mg yeast per tablet.

8. The method of claim 2 wherein the composition is administered shortly after cessation of consumption of alcohol.

9. A method of reducing the intoxicating effects associated with the comsumption of beverage ethyl alcohol by a person which comprises orally administering to said person showing the effects of intoxication a composition consisting esssentially of at least about 30 mg. of thiamine; at least 30 mg. of riboflavin; at least 10 mg. of niacin and yeast in an amount of from 300 to 2000 mg., said thiamine, riboflavin and niacin being present in the ratios of about 3 parts thiamine, 3 parts riboflavin and 1 part niacin.

10. A composition for reducing the intoxicating effects associated with the consumption of beverage ethyl alcohol by humans, which composition consists essentially of thiamine, riboflavin and niacin in amounts of at least about 30 mg. of thiamine; at least about 30 mg. of riboflavin, at least about 10 mg. of niacin and up to about 2000 mg. of yeast per dosage unit.

11. A composition according to claim 10 which contains from about 30 to 200 mg. thiamine, from about 30 to 200 mg. of riboflavin and from about 10 to 80 mg. of niacin.

12. A composition according to claim 10 wherein the thiamine, riboflavin and niacin are present in ratios of about 3 parts thiamine, 3 parts riboflavin and 1 part niacin.

13. A composition according to claim 10 which contains a dosage unit consisting essentially of 30 to 200 mg. thiamine, 30 to 200 mg. of riboflavin, 10 to 80 mg. of niacin and up to 2000 mg. of yeast, said thiamine, riboflavin and niacin being present in ratios of 3 parts thiamine, 3 parts riboflavin and 1 part niacin.

14. A composition according to claim 10 which contains from about 800 to 1600 mg. of edible yeast.

15. The composition of claim 10 wherein the amount of thiamine is from 120 to 140 mg, the amount of riboflavin is from 120 to 140 mg, the amount of niacin is from 35 to 45 mg, and the amount of yeast is from 800 to 1600 mg.

16. The composition of claim 15 wherein the amount of thiamine is 120 mg, the amount of riboflavin is 120 mg, the amount of niacin is 40 mg, and the amount of yeast is 1,200 mg, and wherein said composition is in the form of four tablets.

17. The composition of claim 15 wherein the composition is in the form of four tablets, and each tablet consists of 35 mg thiamine, 35 mg riboflavin, 10 mg niacin, 300 mg yeast, and inert tableting aids.

18. A composition according to claim 10 which contains a dosage unit consisting essentially of from 30 to 200 mg. of thiamine, 30 to 200 mg. of riboflavin, 10 to 80 mg. of niacin and from about 300 to 2000 mg. of yeast, said thiamine, riboflavin and niacin being present in said dosage unit in the respective ratios of about 3 parts thiamine, 3 parts riboflavin and 1 part niacin.

* * * * *